(12) United States Patent
Holl et al.

(10) Patent No.: US 6,303,018 B1
(45) Date of Patent: Oct. 16, 2001

(54) METHOD AND APPARATUS FOR DETERMINING $O_2$ AND $N_2O$ IN GAS MIXTURES

(75) Inventors: Konrad Holl, Aalen-Dewangen; Dejan Ilic, Ellwangen; Michael Schmalz, Ellwangen-Eggenrot; Hans-Joachim Kohnke, Kassel, all of (DE)

(73) Assignee: Varta Geratebatterie GmbH (DE)

( * ) Notice: Subject to any disclaimer, the term of this patent is extended or adjusted under 35 U.S.C. 154(b) by 0 days.

(21) Appl. No.: 09/425,104

(22) Filed: Oct. 13, 1999

(30) Foreign Application Priority Data

Oct. 16, 1998 (DE) .............................. 198 47 707

(51) Int. Cl.[7] .................................................. G01N 27/403
(52) U.S. Cl. .................... 205/781; 205/783; 204/406; 204/415; 204/432; 204/431
(58) Field of Search .................................. 205/781, 783; 204/406, 415, 431, 432; 73/23.3, 23.31, 23.32

(56) References Cited

U.S. PATENT DOCUMENTS

| | | | |
|---|---|---|---|
| Re. 31,914 | * | 6/1985 | Oswin et al. ........................ 204/412 |
| 3,622,487 | * | 11/1971 | Chand ................................. 205/781 |
| 3,763,025 | * | 10/1973 | Chand ................................. 205/781 |
| 4,132,616 | * | 1/1979 | Tantram et al. ..................... 204/415 |
| 4,400,242 | * | 8/1983 | Albery et al. ....................... 204/415 |
| 4,495,051 | * | 1/1985 | Fujita et al. ........................ 204/408 |
| 4,581,121 | * | 4/1986 | Dailey et al. ....................... 204/406 |
| 4,914,424 | * | 4/1990 | Hirao et al. ........................ 340/632 |
| 4,956,063 | * | 9/1990 | Hale ................................... 204/401 |
| 5,902,467 | * | 5/1999 | Wang et al. ........................ 204/415 |

FOREIGN PATENT DOCUMENTS

35186 * 9/1997 (WO) .

* cited by examiner

Primary Examiner—Robert J. Warden, Sr.
Assistant Examiner—Kaj K. Olsen
(74) Attorney, Agent, or Firm—Schnader Harrison Segal & Lewis LLP

(57) ABSTRACT

A method for determining relative amounts of $O_2$ and $N_2O$ in gas mixtures by quantitative electrochemical reaction including feeding a gas mixture containing $O_2$ and $N_2O$ to a zinc-air cell having electrodes connected to a circuit consisting of a plurality of diodes and resistors, which circuit is set to have an electrochemical working range corresponding to each of the $O_2$ and $N_2O$; and measuring current flowing in the respective working range to determine the relative proportions of $O_2$ and $N_2O$ in the gas mixture.

An electrochemical cell including a casing capable of containing a gas mixture, including $O_2$ and $N_2O$ a zinc-air cell in the casing, and a circuit connected to electrodes of the zinc-air cell, the circuit containing a plurality of diodes, resistors and tap points; means for measuring current to determine the relative proportions of $O_2$ and $N_2O$ in the gas mixture.

4 Claims, 2 Drawing Sheets

METHOD AND APPARATUS FOR DETERMINING $O_2$ AND $N_2O$ IN GAS MIXTURES

FIELD OF THE INVENTION

This invention relates to a method and device for the determination of oxygen ($O_2$) and nitrous oxide ($N_2O$) concentrations in gas mixtures by quantitative electrochemical reaction.

RELATED ART

U.S. Pat. No. Re 31,914 discloses an electrochemical method for the determination of toxic gases in air. Further, U.S. Pat. Nos. 4,495,051, 4,894,138 and 4,914,424 describe galvanic cells which are used as oxygen sensors. In particular, WO 97/35186 discloses a method and a device for determining the proportion of oxygen in the breathing air delivered in medical ventilation devices. In this case, an alkaline zinc-air cell is used as a sensor.

Alkaline zinc-air cells are made as button cells on a mass-production scale worldwide and are used as primary cells, in particular, in hearing aids. If the supply of oxygen is restricted by flow and/or diffusion obstacles, then the maximum deliverable current becomes the limiting current and then depends only on the oxygen concentration in the medium next to the $O_2$ cathode. The zinc-air cell thereby becomes a sensor cell for oxygen concentration measurement or oxygen quantity measurement when used in closed volume.

When monitoring patients' breathing air in nitrous oxide anesthesia, it has been found that it is not sufficient merely to measure the oxygen content, but it is also necessary to control the nitrous oxide concentration.

OBJECTS

An object of the invention is accordingly to provide a method and device for the determination of oxygen ($O_2$) and nitrous oxide ($N_2O$) concentrations in gas mixtures, with which oxygen and nitrous oxide in breathing air can be determined in tandem.

SUMMARY OF THE INVENTION

The electrochemical working ranges are set by setting voltage ranges. This being the case, a lower voltage range of about 0.4 to 0.8 V and an upper voltage range of about 0.8 and 1.5 V are set. The virtually simultaneous determination of nitrous oxide and oxygen is preferably achieved by temporarily bypassing a diode to set the lower voltage range.

The device according to the invention for carrying out the method includes a casing which accommodates the gas mixtures, a zinc-air cell, and a circuit which is connected to the electrodes of the zinc-air cell and contains diodes and resistors as well as tap points and arrangements for measuring and indicating the current value. The circuit preferably contains a periodically actuable bypass switch which is connected in parallel with at least one of the diodes. In one embodiment of the circuit, the diodes are Zener diodes.

DETAILED DESCRIPTION OF THE INVENTION

Figure 1:
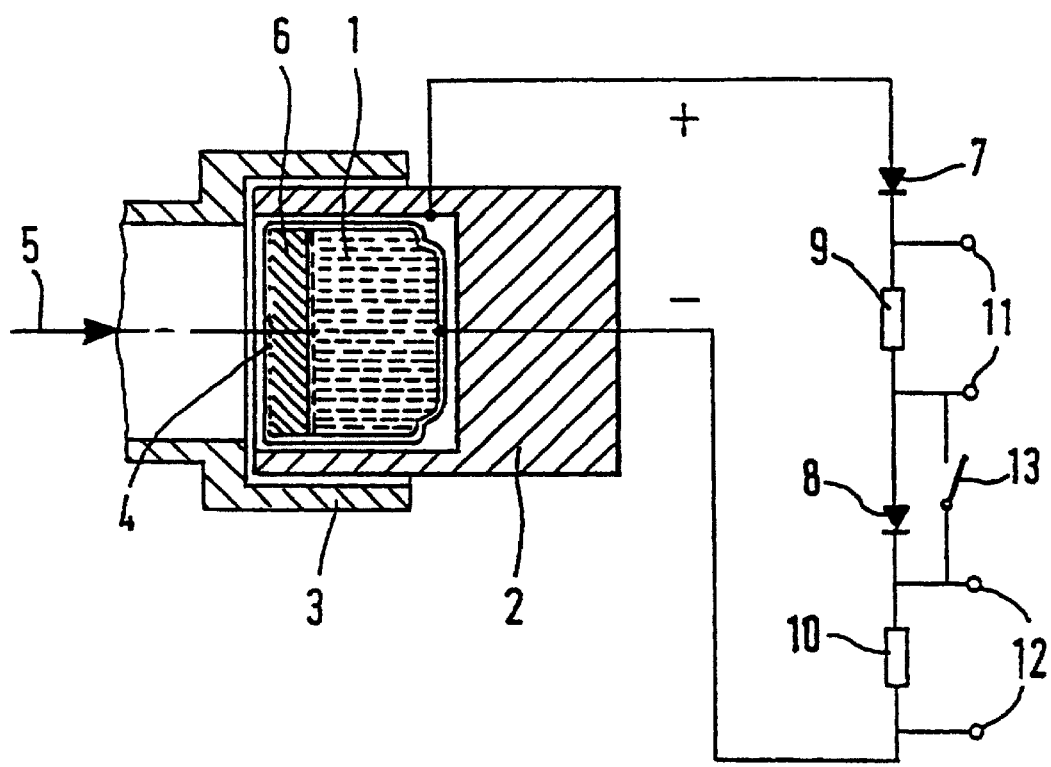
FIG. 1 shows a measuring device according to the invention having a circuit by which two voltage windows are produced.

It will be appreciated that the following description is intended to refer to specific embodiments of the invention selected for illustration in the drawings and is not intended to define or limit the invention, other than in the appended claims.

Comprehensive experimental studies have shown that nitrous oxide behaves inertly at the oxygen electrode of a zinc-air cell with active carbon as a catalyst. Only on electrodes made of silver or silver-catalyzed carbon and on electrodes with platinum as catalyst is cathodic reduction of nitrous oxide, in which nitrogen is obtained as a reaction product, encountered in the voltage range between 0.45 V and 0.9 V. In this range, however, oxygen also reacts.

To achieve the object of determining the concentration of oxygen and nitrous oxide in a mixed gas using one cell, the following method was developed. It is defined by the voltage range of a cell with a zinc anode and a gas cathode in alkaline solution. Below a voltage of 0.4 V, in an inert atmosphere, an electric current flows with cathodic hydrogen evolution at the gas electrode. When nitrous oxide is present, it is cathodically reduced, and the flow of current ends at about 0.9 V. At high voltages, the nitrous oxide is inert. When oxygen is present, is it is reduced in the entire voltage range up to about 1.45 V. Beyond 1.6 V oxygen is also inert.

According to the invention, oxygen and nitrous oxide are determined in tandem in the breathing air fed to a cell by successively carrying out two current measurements in different voltage windows. A second voltage window picks up the voltage range from about 0.4 V to 0.8 V, and a first voltage window picks up the about 0.8–1.5 V voltage range.

According to the drawing, a commercially available zinc-air button cell 1 is contained a holder 2. The holder 2 is placed in a gas sample space 3 (only partially represented) in such a way that the gas inlet opening 4 of the zinc-air button cell 1 faces the gas sample space 3. The gas mixture 5, which essentially contains nitrogen, oxygen, nitrous oxide and carbon dioxide is, therefore, in contact with the gas cathode 6 of the zinc-air button cell 1. The circuit connected to the zinc-air button cell 1 consists of diodes 7, 8, preferably Zener diodes, and resistors 9, 10. The diodes 7 and 8 define the first voltage window, which is evaluated at tap points 11. A bypass switch 13 is further provided. Using the bypass switch 13, the diode 8 can be bypassed so that diode 7 alone then defines the second voltage window for the gas cell. As soon as oxygen is present, a current can be measured in the first voltage window at the tap points 11 and in the upper second voltage window at the tap points 12, this current being of the same value in both voltage windows when nitrous oxide is absent, if the limit current condition is satisfied. If only nitrous oxide is present, then current flows only in the second voltage window, and the first voltage window remains free of current. If nitrous oxide and oxygen are present, then different currents flow in the two voltage windows, and the concentration of oxygen and nitrous oxide in the gas mixture can be determined by this by (for example weighted) subtraction.

Actuating the switch 13 makes it possible to change from one voltage window to the other. In order to set up the steady-state current, the measuring arrangement requires a certain length of time, which is dictated by the time constraints of the mechanical and electrochemical processes and, therefore, by the design conditions. If the switch 13 is switched to and from with a certain frequency as a flip-flop, then a current signal with a DC and an AC amplitude is created. The latter is a measure of the proportion of nitrous oxide.

The sensor cell is preferably manufactured with parts such as a lid, gasket, and cup of a commercial zinc-air button cell of IEC size 675. Transport of oxygen is limited by a diffusion barrier leading to a dependence current from the oxygen and $N_2O$ gas concentration. Preferably, the diffusion barrier is built by using cups with very small hole sizes, i.e., about 20 to 200 μm. Especially about 50 to 100 μm hole size lead to a limiting current 2 mA and 4 mA, respectively, with the described electrode. Also possible is the use of more air holes of smaller sizes to achieve a better distribution of the oxygen at the electrode leading to faster response time. It is further possible to make a diffusion barrier by using membranes of reduced gas permeability. The electrodes differ from commercial zinc-air electrodes by activated carbon of high selectivity activity on oxygen reduction.

Figure 2:
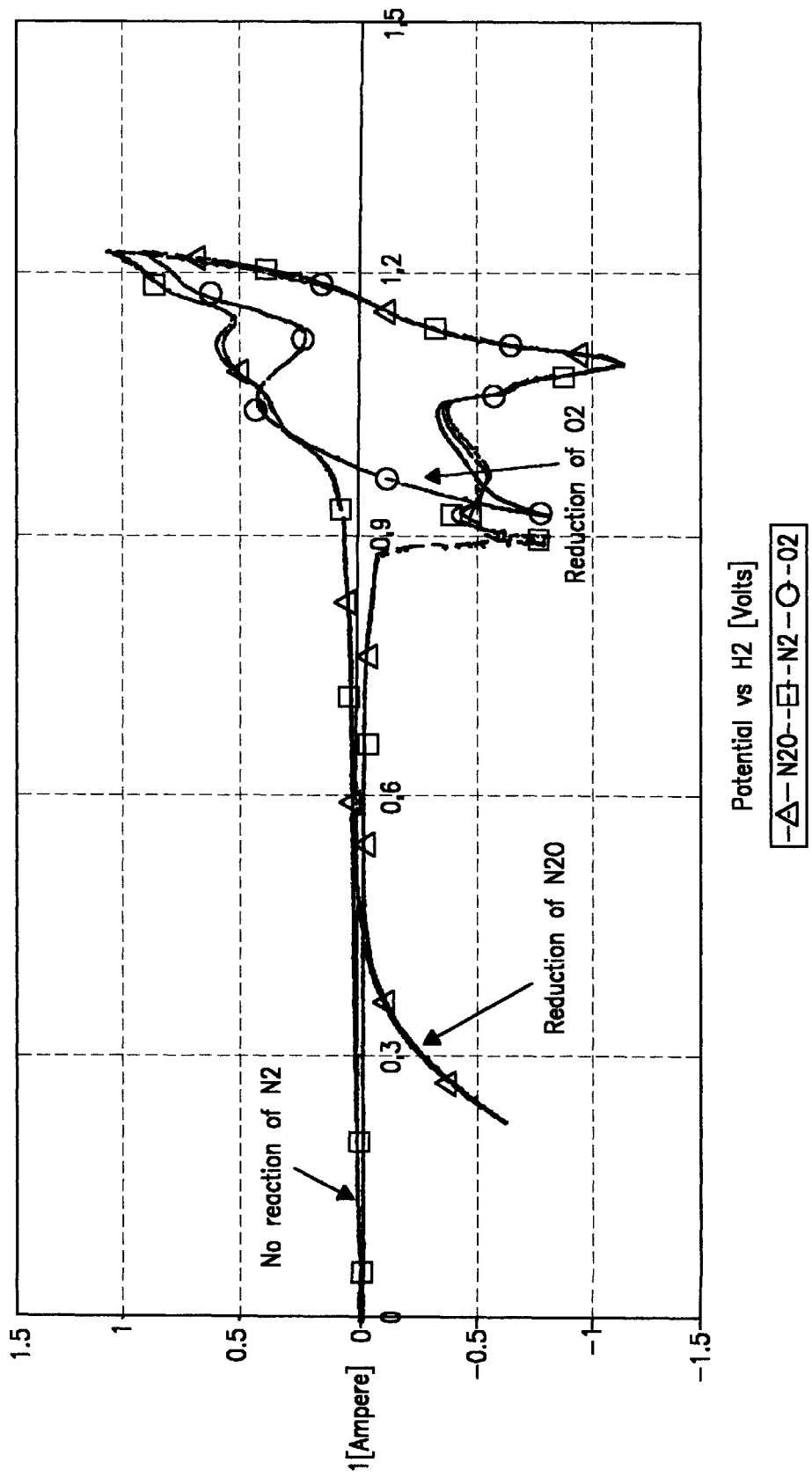
FIG. 2 is a graph potential versus Hz (volts) versus current (amps).

Adding catalysts such as platinum and silver to the electrode makes detection of $N_2O$ and $O_2$ at different voltage windows possible. This is shown in FIG. 2. Nitrogen is always inert. Laughing gas ($N_2O$) is consumed below a potential 0,5 volts versus hydrogen (about 0,9 volts versus zinc).

As an anode material, use of zinc in a mixture of gelling agents like CMC and electrolyte (KOH) has proven to be especially advantageous.

Although this invention has been described in connection with specific forms thereof, it will be appreciated that a wide array of equivalents may be substituted for the specific elements described herein without departing from the spirt and scope of the invention as described in the appended claims.

We claim:

1. A method for determining relative amounts of $O_2$ and $N_2O$ in gas mixtures by quantitative electro-chemical reaction, comprising the steps of:
   feeding a gas mixture containing at least one of $O_2$ and $N_2O$ to a zinc-air cell having an anode and cathode connected to a circuit, said circuit comprising
      at least one first diode;
      at least one resistor;
      at least one second diode;
      a switch; and
      at least one tap point;
   wherein said at least one first and second diodes are in series with said at least one resistor;
   wherein said at least one tap point is across said at least one resistor;
   wherein said switch is in parallel with said at least one second diode to selectively bypass said at least one second diode, for selectively achieving first and second voltage ranges;
   wherein said at least one resistor comprises first and second resistors and said at least one tap point comprises first and second tap points, wherein said first resistor is connected in series to the at least one first diode and said second resistor is connected in series to the at least one second diode, wherein said first tap point is across said first resistor and said second tap point is across said second resistor;
   wherein $O_2$ and $N_2O$ are detectable in the first voltage range and $O_2$ is detectable in the second voltage range; and
   measuring current flowing through the circuit at each of said first voltage range and said second voltage range, to determine the relative proportions of $O_2$ and $N_2O$ in the gas mixture based on said current measurements.

2. The method of claim 1, wherein the lower voltage range is about 0.4 to about 0.8 V and the upper voltage range is about 0.8 to about 1.5 V.

3. An apparatus for detecting $N_2O$ and $O_2$ comprising:
   a casing for containing a gas mixture;
   a zinc-air cell having a zinc anode and a gas cathode, housed with said case;
   a circuit connected to said zinc-air cell electrodes, said circuit comprising
      at least one first diode;
      at least one resistor;
      at least one second diode;
      a switch; and
      at least one tap point;
   wherein said at least one first and second diodes are in series with said at least one resistor;
   wherein said at least one tap point is across said at least one resistor;
   wherein said switch is in parallel with said at least one second diode to selectively bypass said at least one second diode, for selectively achieving first and second voltage ranges; and
   wherein said at least one resistor comprises first and second resistors and said at least one tap point comprises first and second tap points, wherein said first resistor is connected in series to the at least one first diode and said second resistor is connected in series to the at least one second diode, wherein said first tap point is across said first resistor and said second tap point is across said second resistor.

4. The apparatus of claim 3, wherein the diodes are Zener diodes.

* * * * *